(12) United States Patent
Safai et al.

(10) Patent No.: US 7,623,626 B2
(45) Date of Patent: *Nov. 24, 2009

(54) SYSTEM AND METHODS FOR X-RAY BACKSCATTER REVERSE ENGINEERING OF STRUCTURES

(75) Inventors: Morteza Safai, Seattle, WA (US); Gary E. Georgeson, Federal Way, WA (US); William T. Edwards, Foristell, MO (US)

(73) Assignee: The Boeing Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/366,903

(22) Filed: Feb. 6, 2009

(65) Prior Publication Data

US 2009/0168964 A1   Jul. 2, 2009

Related U.S. Application Data

(63) Continuation of application No. 11/739,835, filed on Apr. 25, 2007, now Pat. No. 7,508,910.

(60) Provisional application No. 60/746,478, filed on May 4, 2006.

(51) Int. Cl.
*G01N 23/203* (2006.01)
(52) U.S. Cl. .......................... 378/87; 378/57
(58) Field of Classification Search ............ 378/57, 378/86–89, 196–198
See application file for complete search history.

(56) References Cited

U.S. PATENT DOCUMENTS

| 4,107,563 A | 8/1978 | Oddell |
| 4,577,337 A | 3/1986 | Light |
| 5,181,234 A | 1/1993 | Smith |

(Continued)

FOREIGN PATENT DOCUMENTS

DE          3142349          5/1983

(Continued)

OTHER PUBLICATIONS

Basak et al.; "A Feature Based Parametric Design Program and Expert System for Design"; 2004; Association for Scientific Research: Mathematical and Computational Applications; vol. 9, No. 3, pp. 359-370.

(Continued)

*Primary Examiner*—Hoon Song

(57) ABSTRACT

A system and methods for x-ray backscatter reverse engineering of structures. One embodiment includes a plurality of articulated arms attached to a movable base. Another embodiment includes a single counterweighted arm attached to a movable base. The arms include x-ray detectors. At least one x-ray source, which may be mounted on the arm(s), emits x-rays, which are backscattered off the surfaces and objects of interest and captured by the detectors to generate images of hidden objects. The present system provides improved speed and resolution over prior art systems. The system has a field-of-view and effective scanning range versatile enough to work in various orientations and in environments of various sizes. In certain embodiments the system is compact and lightweight so that it can be easily transported and used within confined spaces or in environments where weight is a consideration, such as inside or underneath aircraft. The system is also pointable and adaptable.

25 Claims, 4 Drawing Sheets

U.S. PATENT DOCUMENTS

| | | | |
|---|---|---|---|
| 5,243,665 | A | 9/1993 | Maney et al. |
| 5,260,982 | A | 11/1993 | Fujii et al. |
| 5,438,605 | A | 8/1995 | Burke et al. |
| 5,729,620 | A | 3/1998 | Wang |
| 5,763,886 | A | 6/1998 | Schulte |
| 5,923,573 | A | 7/1999 | Hatanaka |
| 6,094,472 | A | 7/2000 | Smith |
| 6,282,260 | B1 | 8/2001 | Grodzins |
| 6,292,533 | B1 | 9/2001 | Swift et al. |
| 6,370,222 | B1 | 4/2002 | Cornick, Jr. |
| 6,424,695 | B1 | 7/2002 | Grodzins et al. |
| 6,501,822 | B2 | 12/2002 | Roder |
| 6,546,072 | B1 | 4/2003 | Chalmers |
| 6,560,315 | B1 | 5/2003 | Price et al. |
| 6,618,465 | B2 | 9/2003 | Mohr et al. |
| 6,637,266 | B1 | 10/2003 | Froom |
| 6,735,279 | B1 | 5/2004 | Jacobs et al. |
| 6,757,353 | B2 | 6/2004 | Furze |
| 6,888,640 | B2 | 5/2005 | Spina et al. |
| 6,950,495 | B2 | 9/2005 | Nelson et al. |
| 6,950,719 | B2 | 9/2005 | Landers et al. |
| 7,024,272 | B2 | 4/2006 | Thomas et al. |
| 7,069,192 | B1 | 6/2006 | Freitag |
| 7,086,028 | B1 | 8/2006 | Davis et al. |
| 7,099,434 | B2 | 8/2006 | Adams et al. |
| 7,103,434 | B2 | 9/2006 | Chernyak et al. |
| 7,203,276 | B2 | 4/2007 | Arsenault et al. |
| 7,218,704 | B1 | 5/2007 | Adams et al. |
| 7,224,772 | B2 | 5/2007 | Jacobs et al. |
| 7,280,990 | B2 | 10/2007 | Turner et al. |
| 7,305,063 | B2 | 12/2007 | Heuscher |
| 7,508,910 | B2 * | 3/2009 | Safai et al. ............... 378/57 |
| 2001/0016803 | A1 | 8/2001 | Sartiono et al. |
| 2002/0123812 | A1 | 9/2002 | Jayaram et al. |
| 2003/0043964 | A1 | 3/2003 | Sorenson |
| 2004/0264626 | A1 | 12/2004 | Besson |
| 2007/0189454 | A1 | 8/2007 | Georgeson et al. |

FOREIGN PATENT DOCUMENTS

| | | |
|---|---|---|
| EP | 1227316 | 7/2002 |
| JP | 04309187 A | 10/1992 |
| JP | 2006040053 A | 2/2006 |
| WO | WO 00/33059 | 6/2000 |
| WO | WO 2007/129249 | 11/2007 |

OTHER PUBLICATIONS

Crews et al.; "X-ray Computed Tomography for Geometry Acquisition"; Mar. 1993, Materials Directorate, Wright Laboratory, Air Force Materiel Command, Wright-Patterson Air Force Base; National Technical Information Service; Published in: US.

Huifen et al.; "Feature-based Collaborative Design"; 2003; Elsevier; Journal of Materials Processing Technology; vol. 139; pp. 613-618.

Lockwood et al.; "Field Tests of X-ray Backscatter Mine Detection", Detection of Abandoned Land Mines, 1998. Second International Conference on the (Conf. Publ. No. 458) Edinburgh, UK Oct. 12-14, 1998, London, UK, IEE, UK, Oct. 12, 1998, pp. 160-163, XP006505028, ISBN: 0-85296-711-X.

Poranski et al.; "X-ray Backscatter Tomography for Nondestructive evaluation at the Naval Research Lab", Proc SPIE Int Soc Opt Eng; Proceedings of SPIE—The International Society for Optical Engineering 1995 Society of Photo-Optical Instrumentation Engineers, Bellingham, WA, USA, vol. 2459, 1995, pp. 70-78, XP002462304.

Sanami et al.; "A Proposal of Assembly Model Framework Specialized for Unified Parametrics", 10$^{th}$ International Conference on Precision Engineering; Yokohama, Japan; Jul. 18-20, 2001; Tokyo University of Agriculture and Technology; Kitajima Laboratory; pp. 962-966.

Shedlock et al.; "Optimization of an RSD x-ray backscatter system for detecting defects in the space shuttle external tank thermal foam insulation", Penetrating Radiation Systems and Applications VII. Edited by Doty, F. Patrick; Barber, H. Bradford; Roehrig, Hans. Proceedings of the SPIE, vol. 5923, pp. 205-216 (2005).

Wang et al.; Geometry-based Semantic ID for Persistent and Interoperable Reference in Feature-based Parametric Modeling; 2005; Elsevier; Computer-Aided Design; vol. 37; pp. 1081-1093.

Yancey; "CT-Assisted Reverse Engineering for Aging Aircraft Resupply"; Mar. 1998; XP002441957.

Z Backscatter; http://www.as-e.com/products_solutions/z_backscatter.asp; American Science and Engineering, Inc. (Image obtained from Internet Archive [http://www.archive.org/index.php] and represents webpage as it appeared on Apr. 4, 2005).

Zhu et al.; "X-ray Compton backscattering techniques for process tomography: imaging and characterization of materials"; Measurement Science and Technology; Mar. 1, 1996; vol. 7, No. 3, pp. 281-286; XP020063979; Institute of Physics Publishing; Bristol; UK.

International Search Report and the Written Opinion of the International searching Authority (EPO) dated Jul. 30, 2007 on related PCT application No. PCT/US2007/003466.

International Search Report on related PCT application No. PCT/US2007/010843 from International Searching Authority (EPO) dated Dec. 12, 2007.

Written Opinion on related PCT application No. PCT/ US2007/010843 from International Searching Authority (EPO) dated Dec. 12, 2007.

International Search Report on related PCT application No. PCT/US2007/010758 from Internatioanl Searching Authority (EPO) dated Jan. 10, 2008.

Written Opinion on related PCT application No. PCT/ US2007/010758 from International Searching Authority (EPO) dated Jan. 10, 2008.

Non-Final Office Action on related U.S. Appl. No. 11/744,115 dated Apr. 15, 2008.

Final Office Action on related U.S. Appl. No. 11/744,115 dated Sep. 16, 2008.

Notice of Allowance on related U.S. Appl. No. 11/744,115 dated Jan. 13, 2009.

Non-Final Office Action on related U.S. Appl. No. 11/352,118 dated Jul. 13, 2006.

Final Office Action on related U.S. Appl. No. 11/352,118 dated Dec. 28, 2006.

Non-Final Office Action on related U.S. Appl. No. 11/352,118 dated Jun. 14, 2007.

Final Office Action on related U.S. Appl. No. 11/352,118 dated Nov. 14, 2007.

Non-Final Office Action on related U.S. Appl. No. 11/352,118 dated Oct. 16, 2008.

Notice of Allowance on related U.S. Appl. No. 11/739,835 dated Nov. 24, 2008.

* cited by examiner

SYSTEM AND METHODS FOR X-RAY BACKSCATTER REVERSE ENGINEERING OF STRUCTURES

CROSS-REFERENCE TO RELATED APPLICATIONS

This application is a continuation of application Ser. No. 11/739,835, filed on Apr. 25, 2007 now U.S. Pat. No. 7,508,910, which claims priority to provisional application Ser. No. 60/746,478, filed on May 4, 2006. The entire contents of the priority applications are hereby incorporated by reference.

BACKGROUND

1. Technical Field

The present invention relates to imaging of objects using x-ray backscattering techniques.

2. Description of Related Art

A large market exists for modification of structures and systems within military and commercial aircraft. The modification process involves reverse engineering of the aircraft to identify structures and systems that are to be modified. One challenge faced by modification engineers is uncertainty about the locations and configurations of structures and systems that are hidden from view. For example, flight-ready, fielded aircraft have many structures and systems that are obscured by exterior skins and interior furnishings and closure panels. Often, legacy data such as drawings, planning and tooling are insufficient to determine present configurations of structures and systems. Legacy data also does not typically include information about hidden foreign objects or debris.

Some conventional techniques for determining the locations and configurations of hidden aircraft structures and systems during modification procedures include digital photography, panoramic cameras, and line-of-sight reverse engineering. These methods have significant drawbacks, such as requiring partial disassembly of the subject aircraft in order to expose the hidden structures/systems. This process is labor intensive and therefore quite expensive. Furthermore, only after the disassembly has been completed can the process of planning the modifications begin. The need for disassembly thus lengthens the timeframe for aircraft modification, which in turn increases the cost of the process. Furthermore, conventional systems and methods lack verified definition data for each aircraft going through modifications.

One method for analyzing structures involves x-ray backscattering. Conventional x-ray backscatter systems comprise an x-ray tube that generates photons, and at least one solid-state detector or photo-multiplier tube. Photons emerge from the source in a collimated "flying spot" beam that scans vertically while the system is moved horizontally. Backscattered photons are collected in the detector(s) and used to generate two-dimensional and/or three-dimensional images of objects hidden behind coverings.

X-ray backscattering systems are currently used to scan trucks and railroad cars for contraband. For example, at a border crossing an x-ray backscatter image may help border officials to spot people or drugs hidden in secret compartments. The systems in use in such applications are mounted in large vans. The collimated beam scans vertically while the van drives alongside the truck or railcar. The detector(s) remain at a constant distance from the scanned object as the van drives.

The large size of these van-mounted systems makes them unsuitable for use in interior spaces, such as inside an aircraft (except, perhaps, inside large cargo aircraft having ramp doors). Furthermore, in order for an x-ray backscatter to produce a distortion-free image, the photon detector must be equidistant from all portions of the object being scanned. Thus, while van-mounted systems are well-adapted for producing images of trucks or railcars, which generally have vertical side walls, aircraft fuselages are generally cylindrical and have oval or elliptical cross-sections. As a collimated beam scans such a surface, some portions of the surface are located closer to the photon detector(s) than other portions. The variations in distance from the detector(s) produce distortions in the backscattered image. Such distortions present a minor inconvenience when searching for contraband, where the goal is merely to identify the presence of foreign objects to determine whether a closer investigation is warranted. In a reverse engineering application, however, distortions present a major problem. Before modification engineers can begin to develop a modification plan, they must have an image that meets a certain threshold in accurately identifying the locations, sizes and configurations of hidden structures and systems. Current systems do not meet this threshold.

Conventional x-ray backscatter systems are also not able to account for objects within an aircraft, such as galleys, cabinets and seats. Further, these systems do not have adequate scanning speed, robustness, ability to work in various orientations, scanning range, or field of view for aircraft reverse engineering applications. They are also not tailored to detect and accurately depict the materials present on aircraft.

SUMMARY

The preferred embodiments of the present system and methods for x-ray backscatter reverse engineering of structures have several features, no single one of which is solely responsible for their desirable attributes. Without limiting the scope of this system and these methods as expressed by the claims that follow, their more prominent features will now be discussed briefly. After considering this discussion, and particularly after reading the section entitled "Detailed Description of the Preferred Embodiments", one will understand how the features of the preferred embodiments provide advantages, which include, without limitation, improved resolution, over prior art systems, high scanning speeds, field-of-view and effective scanning range versatile enough to work in various orientations and in environments of various size, the system is compact and lightweight so that it can be easily transported and used within confined spaces or in environments where weight is a consideration, and the system is both pointable and adaptable.

One aspect of the present system and methods for x-ray backscatter reverse engineering of structures includes the realization that there is a need for a high-speed, high-resolution, portable, articulated, transportable and lightweight x-ray back scattering system that limits image distortion and allows for inspection between structures, such as cabinets, overhead bins, and seats, and is capable of traveling through relatively narrow spaces.

One embodiment of the present system and methods comprises a method of interrogating a surface of a structure using an x-ray backscatter system to generate an image of an object obscured behind the surface. The x-ray backscatter system includes a mobile base portion, at least a first arm secured to the base at an articulation point, at least one x-ray source, and at least one x-ray detector configured to collect x-rays backscattered from the object. The method comprises advancing the system through the structure. The method further comprises articulating the arm and the x-ray detector about the articulation point. The x-ray detector is positioned on the arm at a location spaced from the articulation point. The method further comprises linearly extending and contracting the arm with respect to the mobile base portion. The method further comprises generating x-rays from the x-ray source and directing the x-rays toward the surface. The method further comprises detecting a portion of the x-rays at the x-ray detector after the portion of the x-rays have been backscattered from the object obscured behind tire surface.

Another embodiment of the present system and methods comprises a method of interrogating a surface of a structure using an x-ray backscatter system to generate an image of an object obscured behind the surface. The x-ray backscatter system includes a mobile base portion, at least a first arm secured to the base at an articulation point, at least one x-ray source, and at least one x-ray detector configured to collect x-rays backscattered from the object. The method comprises advancing the system through the structure. The method further comprises articulating the arm and the x-ray detector about the articulation point. The x-ray detector is positioned on the arm at a location spaced from the articulation point. The method further comprises articulating a first segment of the arm with respect to a second segment of the arm, the first and second segments being connected by a joint. The method further comprises generating x-rays from the x-ray source and directing the x-rays toward the surface. The method further comprises detecting a portion of the x-rays at the x-ray detector after the portion of the x-rays have been backscattered from the object obscured behind the surface.

Another embodiment of the present system and methods comprises a method of interrogating a surface of a structure using an x-ray backscatter system to generate an image of an object obscured behind the surface. The x-ray backscatter system includes a mobile base portion, at least a first arm secured to the base at an articulation point, at least one x-ray source, and at least one x-ray detector configured to collect x-rays backscattered from the object. The method comprises advancing the system through the structure. The method further comprises articulating the arm and the x-ray detector about the articulation point. The x-ray detector is positioned on the arm at a location spaced from the articulation point. The method further comprises generating x-rays from the x-ray source and directing the x-rays toward the surface. The method further comprises detecting a portion of the x-rays at the x-ray detector after the portion of the x-rays have been backscattered from the object obscured behind the surface. The arm includes a counterweight at a location spaced from the detector and on an opposite side of the articulation point from the detector.

Another embodiment of the present system and methods comprises a method of interrogating a surface of a structure using an x-ray backscatter system to generate an image of an object obscured behind the surface. The x-ray backscatter system includes a mobile base portion, at least a first arm secured to the base at an articulation point, at least one x-ray source, and at least one x-ray detector configured to collect x-rays backscattered from the object. The method comprises advancing the system through the structure. The method further comprises articulating the arm, the x-ray detector and the x-ray source about the articulation point, the x-ray detector and the x-ray source being positioned on the arm at locations spaced from the articulation point. The method further comprises generating x-rays from the x-ray source and directing the x-rays toward the surface. The method further comprises detecting a portion of the x-rays at the x-ray detector after the portion of the x-rays have been backscattered from the object obscured behind the surface.

BRIEF DESCRIPTION OF THE DRAWINGS

The preferred embodiments of the present system and methods for x-ray backscatter reverse engineering of structures will now be discussed in detail with an emphasis on highlighting the advantageous features. These embodiments depict the novel and non-obvious system and methods shown in the accompanying drawings, which are for illustrative purposes only. These drawings include the following figures, in which like numerals indicate like parts.

DETAILED DESCRIPTION

The present system and methods for x-ray backscatter reverse engineering of structures advantageously provide improved resolution over prior art systems, enabling accurate determination of the locations and configurations of structures and systems obscured by external skins and/or interior closure panels. The system reduces or eliminates the image distortion characteristic of prior art systems. In certain embodiments the system also provides improved resolution even at high scanning speeds. The system has a field-of-view and effective scanning range versatile enough to work in various orientations and in environments of various sizes. In certain embodiments the system is compact and lightweight so that it can be easily transported and used within confined spaces or in environments where weight is a consideration, such as inside or underneath aircraft. Because systems and structures in aircraft environments have various orientations and limitations to access, the system is pointable and adaptable.

The present system is described herein with reference to two example embodiments. Those of ordinary skill in the art will appreciate, however, that these embodiments are merely examples. Alternative configurations from those shown in the attached figures may also embody the advantageous characteristics described above. These alternative configurations are within the scope of the present system.

The present system is further described herein with reference to an aircraft. The present system is well adapted for reverse engineering aircraft, which generally have cylindrical fuselages and typically contain obstacles such as seats, overhead bins, galleys, etc. Those of ordinary skill in the art will appreciate, however, that the present system is also well adapted for reverse engineering a wide variety of structures and/or systems with potentially hidden objects. For example, the present system and methods may be employed in reverse engineering power plants, processing plants, refineries, rockets, automobiles, ships, helicopters, trains, etc. Accordingly, the scope of the present system and methods should not be interpreted as being limited to aircraft applications.

Figure 1:
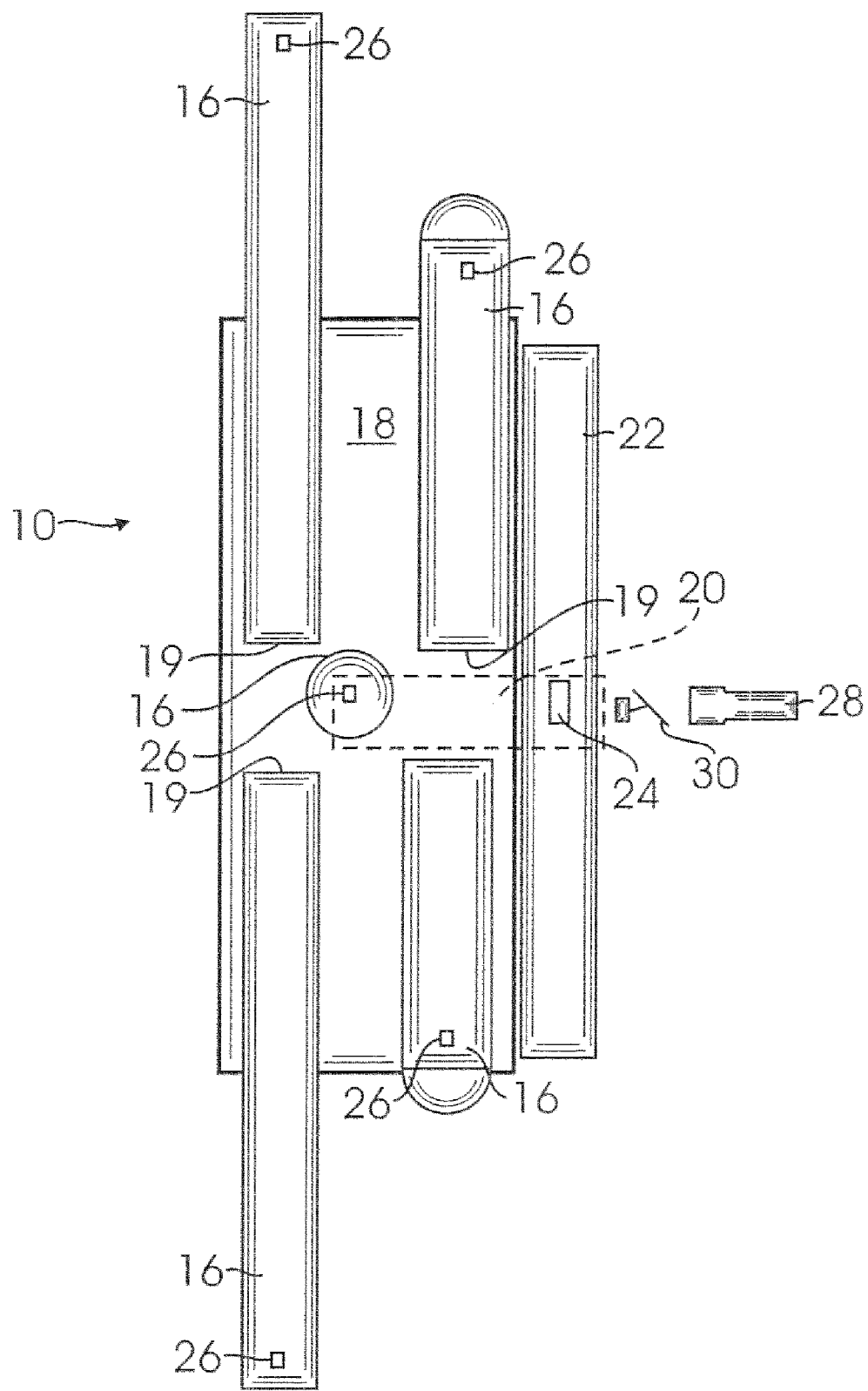
FIG. 1 is a schematic top plan view of one embodiment of the present apparatus for x-ray backscatter reverse engineering of structures.
Figure 2:
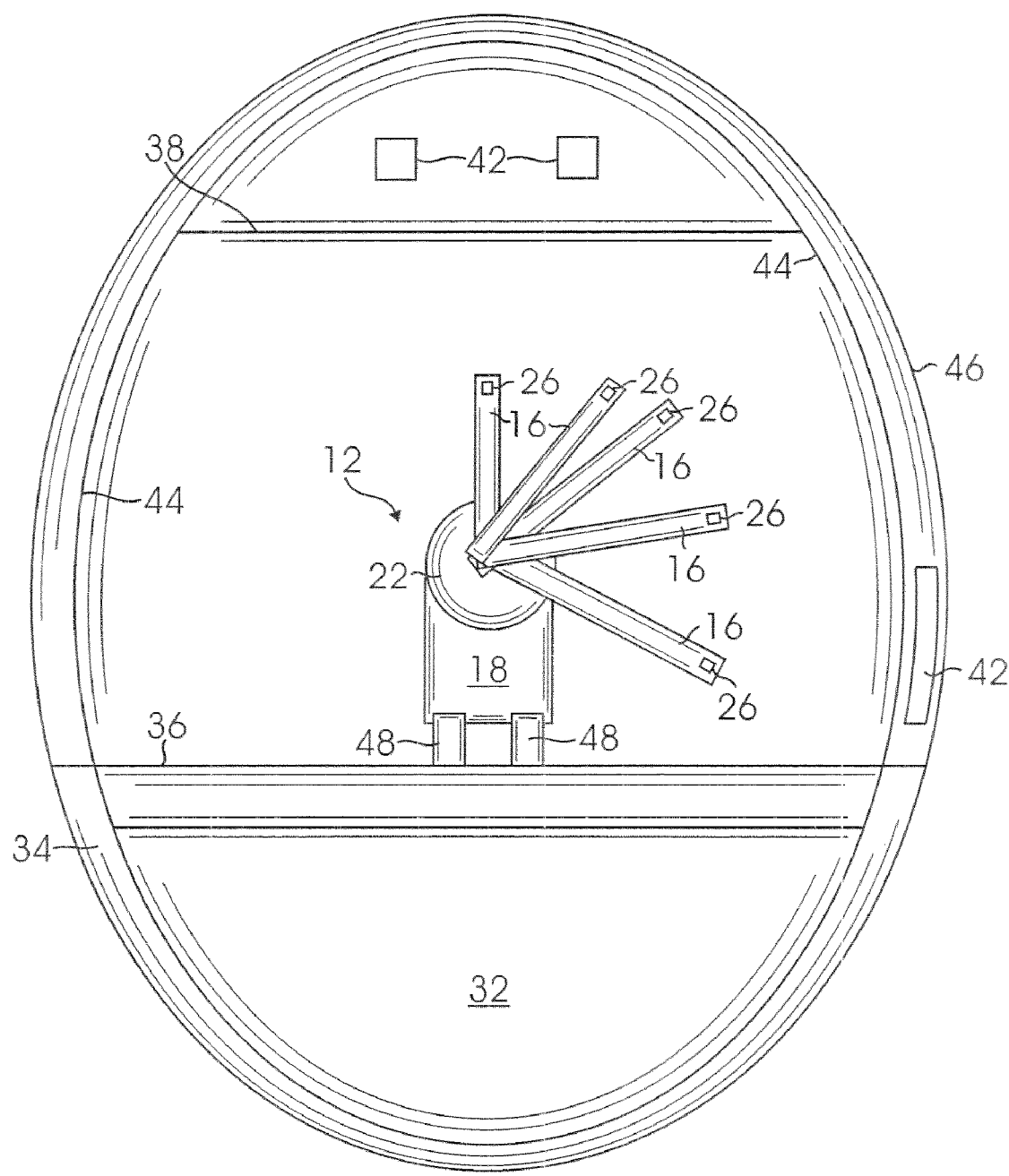
FIG. 2 is a schematic front elevation view of another embodiment of the present apparatus positioned within an aircraft.
Figure 3:
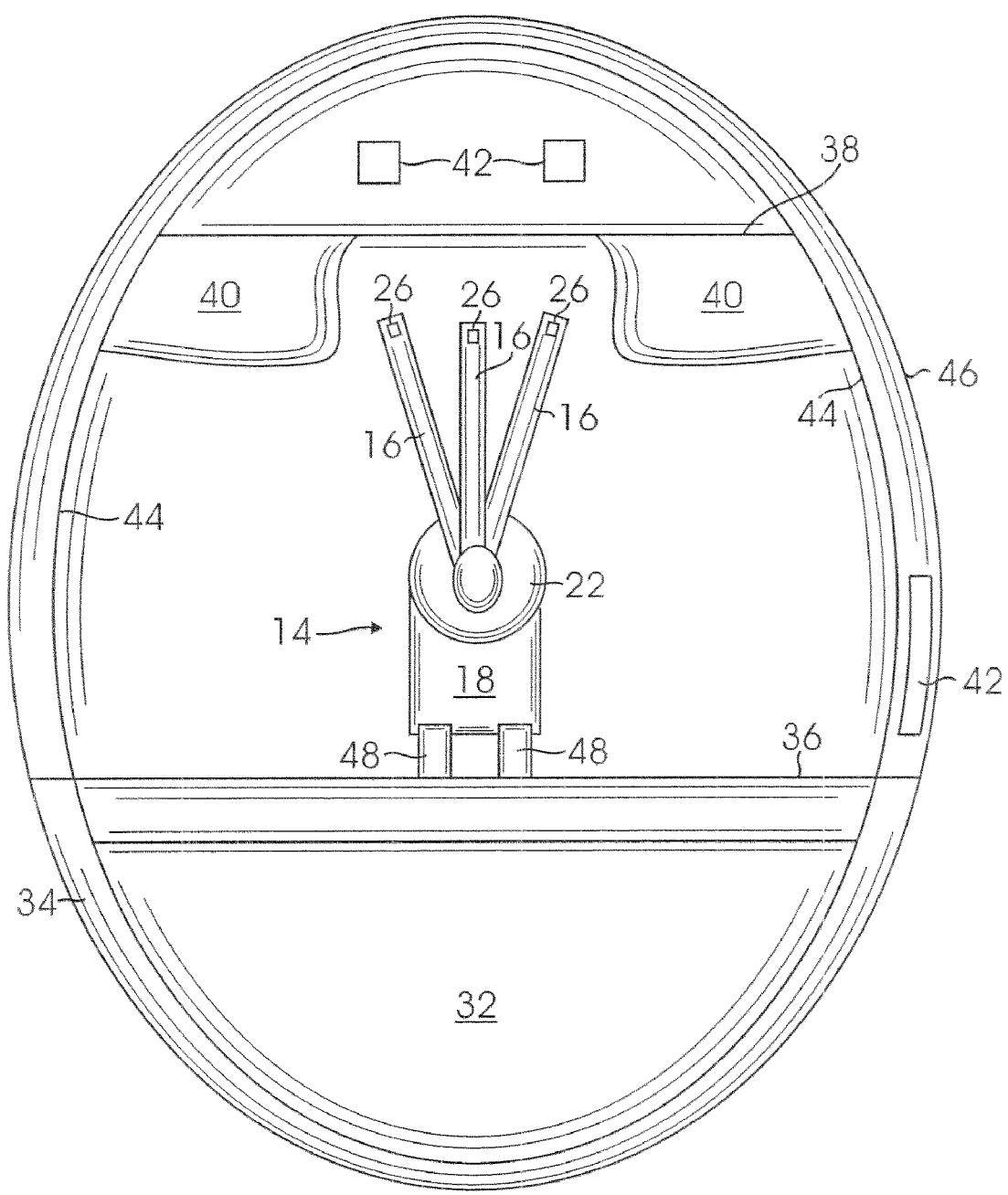
FIG. 3 is a schematic front elevation view of another embodiment of the present x-ray backscatter apparatus positioned within an aircraft and configured to scan between and around overhead storage bins.

With reference to FIGS. 1-3, a first embodiment of the present system 10, 12, 14 comprises an octopus-like configuration having a plurality of articulated arms 16 connected to a base 18. Each of the arms 16 articulates relative to the base 18 about an articulation point 19 (FIG. 1). An x-ray source, which may be an x-ray tube 20 (FIG. 1), generates photons that are directed toward the surfaces to be scanned. A rotating aperture 22 directs the x-rays in a desired pattern. For example, x-rays may emanate from an opening 24 that directs the x-rays as it rotates around an axis of the rotating aperture 22. Detectors 26 positioned on the arms 16 collect photons that are backscattered from the scanned surfaces and from objects hidden behind the scanned surfaces. The detectors 26 assist in generating two-dimensional and/or three-dimensional images of the hidden objects.

In the illustrated embodiment, the x-ray tube 20 is located at the base 18 (FIG. 1). However, those of ordinary skill in the art will appreciate that the x-ray tube 20 could be located elsewhere. For example, one or more of the arms 16 could include x-ray tubes. Positioning x-ray tubes on the arms 16, rather than on the base 18, provides certain advantages as discussed below with respect to the embodiment of FIG. 4. The x-ray tube(s) 20 may include apparatus (not shown) associated with a typical x-ray tube, such as apparatus to prevent the tube from overheating. The base 18 may also include a charge-coupled device (CCD) or complementary metal-oxide-semiconductor (CMOS) with FED lighting and a wide-angle lens 28 and/or scanning mirror 30 (FIG. 1) in order to generate a visual image of the interrogated surface that can be super-imposed on the backscattered images of any hidden objects.

In FIGS. 2 and 3 the embodiments of the present x-ray scanning system 12, 14 are shown within an aircraft 32 including a fuselage 34. The aircraft 32 also includes floor panels 36, ceiling panels 38, and various internal structures, such as overhead storage bins 40 (FIG. 3). As explained in further detail below, the embodiments of the present system 10, 12, 14 are adapted to scan an aircraft (and other structures as detailed above) both from within, as illustrated, and from without. The system is adapted to generate images of objects and systems 42 hidden behind closure panels, such as floor panels 36, ceiling panels 38 and panels attached to interior wall surfaces 44. When scanning from without the aircraft 32, the system is adapted to generate images of objects and systems 42 hidden behind external skins 46.

With reference to FIGS. 2 and 3, the base 18 may include wheels, runners or other apparatus to enable the system to be easily moved. In the illustrated embodiments the bases include wheels 48. In some embodiments the system may include a portable track (not shown) that is assembled and placed on the floor of the aircraft 32. The wheels 48 on the base 18 engage track rails and the base 18 rolls along the track as it scans the aircraft 32 from one end to the other, or as it scans a more limited area of interest. The base 18 may include a motorized drive, and the system may be controlled remotely by a human operator. Alternatively the system may be self-propelled, and may be preprogrammed to follow a desired scanning pattern so that it can operate by itself. The system may include one or more proximity sensors to enable the system to dodge obstacles, such as galleys (not shown) and overhead storage bins 40 (FIG. 3).

In certain embodiments the system is relatively compact so that it is readily transportable and adapted to work within confined spaces, such as within an aircraft or beneath an aircraft wing. For example, in certain embodiments the total envelope size of the system may be 0.5 m×1.0 m×1.0 m. Further, commercial aircraft typically include rows of seats with a relatively narrow aisle dividing adjacent rows. In certain embodiments the base 18 is narrow enough so that the system may move through an aisle without the need to remove any seats from the aircraft.

In certain embodiments the system is relatively lightweight to further facilitate its transportation, and to enable it to work in environments where weight is a consideration. For example, in order to scan an aircraft from the exterior, the system may be placed on a lift having a maximum load capacity.

With reference to FIG. 2, the illustrated system includes five arms 16 and each arm 16 includes a detector 26 at or near an end thereof spaced from the base 18. Those of ordinary skill in the art will appreciate that fewer or more arms 16, and fewer or more detectors 26, could be provided. For example, the embodiment of FIG. 3 includes three arms 16. Those of ordinary skill in the art will also appreciate that in certain embodiments one or more arms 16 might not include a detector 26. However, as discussed in detail below, the system is advantageously capable of scanning a given area in a shorter amount of time as the number of arms 16 with detectors 26 increases.

In certain embodiments, such as those illustrated in FIGS. 2 and 3, each arm 16 is pivotable with respect to the base 18. However, in some embodiments there may be at least one arm 16 that cannot pivot with respect to the base 18. The pivotability of each arm 16 may be limited to rotation about a single axis, or it may include rotation about two or three axes. In certain embodiments the arms 16 may be capable of sweeping through 360° with respect to a horizontal axis passing through the base 18. In such embodiments the system is advantageously able to sweep an entire aircraft interior in only one pass. In other embodiments the arms 16 may be capable of sweeping through lesser angles. For example, in certain embodiments each arm 16 may be capable of sweeping through 180° with respect to a horizontal axis passing through the base 18. To fully scan an aircraft interior with such an embodiment, the base 18 may begin at a first end of the aircraft and move through the interior, toward the opposite end, while the arms 16 sweep and scan to one side. The base 18 may then turn around and move back toward the first end of the aircraft while the arms 16 sweep and scan to the opposite side.

In some embodiments, such as those illustrated in FIGS. 2 and 3, the arms 16 are also linearly extensible and contractible. For example, each arm 16 may telescope. The pivotability and/or extensibility/contractibllity of each arm 16 allows the detector 26 on each arm 16 to be pointable. That is, each detector 26 can be positioned at any of a wide range of orientations and distances from the base 18 without the need to move or adjust the base 18. Each detector 26 can, for example, be lowered to capture images between seats or cabinets (not shown). Each detector 26 can also be raised to obtain images between overhead storage bins 40 or in wheel wells.

The arms 16 can also sweep across surfaces to be interrogated either while the base 18 remains stationary or while the base 18 moves. For example, in FIG. 2 the arms 16 may sweep across the floor panels 36, ceiling panels 38 and interior wall panels 44 in a clockwise or counterclockwise direction while the base 18 moves along the longitudinal axis of the aircraft 32. The base 18 may move continuously while the arms 16 sweep continuously, or the base 18 may move in intervals with the arms 16 performing a full side-to-side sweep between each interval. The arms 16 are also adaptable in that they can pivot and/or extend/contract to avoid or extend around obstacles, such as seats, overhead bins 40 (FIG. 3) and galleys, as discussed further below. In some embodiments, some or all of the arms 16 may include proximity sensors (not shown) that enable the arm(s) 16 to avoid obstacles while scanning.

Pivotability and/or extensibility/contractibility of each arm 16 is of particular advantage when interrogating curved or contoured surfaces, or when interrogating surfaces that include features such as undulations, protrusions, etc. As shown in FIG. 2, for example, the fuselage 34 of a typical aircraft 32 is generally cylindrical, and has an oval or elliptical cross-section. With the system of FIG. 2 the pivotable and extensible/contractible arms 16 can be positioned so that all detectors 26 are substantially equidistant from their respective interrogation surfaces.

A pivotable and extensible/contractible arm 16 is also advantageously able to ensure that the detector 26 on that arm 16 remains at a constant distance from its interrogation surface. As the arm 16 sweeps across a surface, rotation and extension/contraction of the arm 16 maintains the constant distance between the detector 26 and the interrogation surface, even if the surface includes curves, contours, undulations, protrusions, etc. Maintaining a uniform distance reduces the image distortion described above in the section entitled "Description of Related Art". The lack of image distortion facilitates direct comparison of the backscattered image to other data, such as two-dimensional photographs of interior closure panels in an aircraft. Again, in some embodiments some or all of the arms 16 may include proximity sensors. The proximity sensor(s) can aid the arm(s) 16 in maintaining the advantageous uniform distance while scanning.

With reference to FIG. 3, the pivoting and extension/contraction of each arm 16 also allows the present system to scan a given space, such as an aircraft interior, while avoiding obstacles in the space, such as overhead bins 40. In FIG. 3 the arms 16 are positioned to scan the ceiling panels 38 of the aircraft 32 while avoiding obstructions, such as overhead bins 40 and cabinets. The movability of the arms 16 with respect to the base 18 advantageously allows the arms 16 to avoid such obstacles.

As discussed above, the embodiments of FIGS. 2 and 3, which include multiple arms 16, are advantageously able to scan a given surface area quickly. For example, the embodiment of FIG. 3 includes three arms 16. Therefore, this embodiment can scan a given surface area three times faster than an otherwise identical system that includes only one arm 16. Similarly, the embodiment of FIG. 2 can scan a given surface area five times faster than an otherwise identical system that includes only one arm 16. And the multi-arm embodiments can provide the increased scanning speed without sacrificing image resolution. When comparing a three-arm system to a single-arm system, each arm in the three-arm system can move at the same speed as the one arm 16 in the single-arm system (thus preserving image resolution) and yet the three-arm system will cover three times as much surface area in a given interval.

In certain embodiments the base 18 may have additional degrees of freedom besides the ability to roll or slide across a surface. For example, the base 18 may be rotatable about a vertical axis. The base 18 may also be translatable along a vertical axis. That is, the base 18 may include lifting apparatus to raise the articulation point of each arm 16 with respect to a surface on which the base 18 rests.

Figure 4:
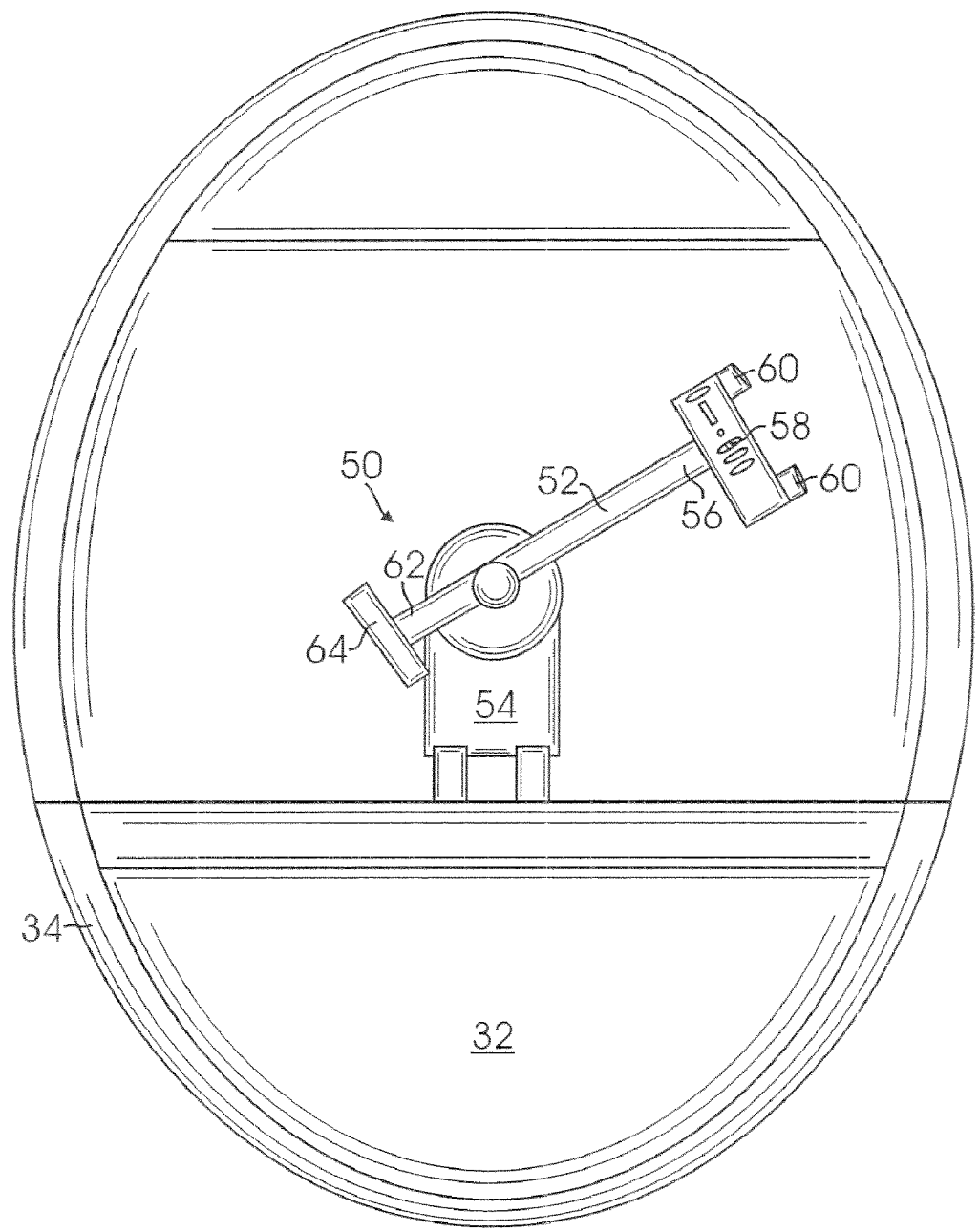
FIG. 4 is a schematic front elevation view of another embodiment of the present x-ray backscatter apparatus positioned within an aircraft.

FIG. 4 illustrates another embodiment of the present system 50. The embodiment of FIG. 4 may include some or all of the features and advantages described above with respect to the embodiments 10, 12, 14 of FIGS. 1-3, such as portability, adaptability, compact size, etc. Accordingly, those features and advantages will not be discussed here.

In FIG. 4, the system 50 includes a single articulated arm 52 attached to a base 54. However, those of ordinary skill in the art will appreciate that more arms 52 may be provided. The arm 52 is pivotable with respect to the base 54, and is also linearly extensible and contractible. A first end 56 of the arm 52 includes an x-ray tube 58 and two detectors 60. However, those of ordinary skill in the art will appreciate that fewer or more detectors 60 may be provided. At a second end 62, opposite the first end 56, the arm 52 includes a counterweight 64 that assists the arm 52 to swing like a pendulum with respect to the base 54. The arm 52 can thus swing back and forth across the interior of the aircraft 32 as the base 54 moves through the aircraft.

The embodiment of FIG. 4 advantageously positions the x-ray tube 58 at or near the end of the arm 52, enabling the x-ray tube 58 to be located close to the interrogation surfaces. This close proximity to the interrogation surfaces reduces beam spread problems, increases photon counts at the detectors 60, and enables the x-ray power to be reduced, which in turn reduces the risk of humans being exposed to harmful radiation. Further, because the x-ray tube 58 and detectors 60 are close to the interrogation surfaces, there is less of a time delay between the moment that an x-ray leaves the x-ray tube 58 and the moment it is detected. The system is thus able to cover more surface area in less time. Reducing the size and power of the x-ray tube 58 also makes it easier to cool the x-ray tube 58 and reduces the cost of the x-ray tube 58. Positioning the detector(s) 60 near the interrogation surfaces also increases the sharpness and resolution of the scanned image, which increases the quality of the reverse engineering data.

Figure 5:
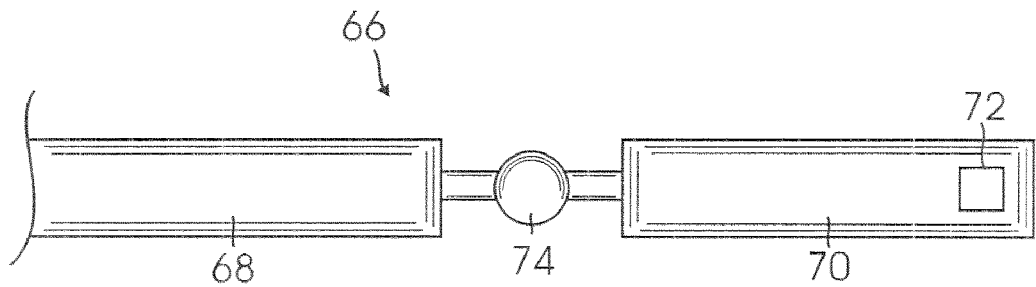
FIG. 5 is a schematic top plan view of one embodiment of a jointed arm for use with the present apparatus for x-ray backscatter reverse engineering of structures.

FIG. 5 illustrates an alternative embodiment of an arm 66 including a first segment 68 and a second segment 70. The first segment 68 is secured to a base (not shown) as described above. An end of the second segment 70 remote from the base includes an x-ray detector 72, and may also include an x-ray source (not shown). A joint 74 connects the first segment 68 and the second segment 70. The joint may have anywhere from one to six degrees of freedom to enable articulation of the second segment 70 with respect to the first segment 68. An embodiment of the present system that includes the jointed arm 66 thus increases the portability and adaptability of the present system.

The embodiments of the present system and methods for x-ray backscatter reverse engineering of structures advantageously enable imaging and analysis of aircraft and other structures without the need for disassembly. The present system and methods thus reduce the time needed to complete aircraft modifications and the associated cost. For example, modification designers are advantageously able to create complete designs before the aircraft is interred for modification.

The above presents a description of the best mode contemplated for carrying out the present system and methods for x-ray backscatter reverse engineering of structures, and of the manner and process of making and using them, in such full, clear, concise, and exact terms as to enable any person skilled in the art to which they pertain to make this system and use these methods. This system and these methods are, however, susceptible to modifications and alternate constructions from those discussed above that are fully equivalent. Consequently, this system and these methods are not limited to the particular embodiments disclosed. On the contrary, this system and these methods cover all modifications and alternate constructions coming within the spirit and scope of the system and methods as generally expressed by the following claims, which particularly point out and distinctly claim the subject matter of the system and methods.

What is claimed is:

1. A method of interrogating a surface of a structure using an x-ray backscatter system to generate an image of an object obscured behind the surface, the x-ray backscatter system including a mobile base portion, at least a first arm secured to the base at an articulation point, at least one x-ray source, and at least one x-ray detector configured to collect x-rays backscattered from the object, the method comprising:
   a) advancing the system through the structure;
   b) articulating the arm and the x-ray detector about the articulation point, the x-ray detector being positioned on the arm at a location spaced from the articulation point;
   c) linearly extending and contracting the arm with respect to the mobile base portion;
   d) generating x-rays from the x-ray source and directing the x-rays toward the surface; and
   e) detecting a portion of the x-rays at the x-ray detector after the portion of the x-rays have been backscattered from the object obscured behind the surface.

2. The method of claim 1, wherein steps a) through e) are performed simultaneously.

3. The method of claim 1, wherein articulating the arm and the x-ray detector about the articulation point comprises rotating the arm and the x-ray detector about at least two axes of rotation.

4. The method of claim 1, further comprising articulating a second arm and a second x-ray detector about a second articulation point on the base, the second x-ray detector being positioned on the second arm at a location spaced from the second articulation point.

5. The method of claim 4, wherein the first and second arms articulate independently of one another.

6. The method of claim 1, further comprising capturing images of the surface using a visual camera.

7. A method of interrogating a surface of a structure using an x-ray backscatter system to generate an image of an object obscured behind the surface, the x-ray backscatter system including a mobile base portion, at least a first arm secured to the base at an articulation point, at least one x-ray source, and at least one x-ray detector configured to collect x-rays backscattered from the object, the method comprising:
   a) advancing the system through the structure;
   b) articulating the arm and the x-ray detector about the articulation point, the x-ray detector being positioned on the arm at a location spaced from the articulation point;
   c) articulating a first segment of the arm with respect to a second segment of the arm, the first and second segments being connected by a joint;
   d) generating x-rays from the x-ray source and directing the x-rays toward the surface; and
   e) detecting a portion of the x-rays at the x-ray detector after the portion of the x-rays have been backscattered from the object obscured behind the surface.

8. The method of claim 7, wherein steps a) through e) are performed simultaneously.

9. The method of claim 7, wherein articulating the arm and the x-ray detector about the articulation point comprises rotating the arm and the x-ray detector about at least two axes of rotation.

10. The method of claim 7, further comprising articulating a second arm and a second x-ray detector about a second articulation point on the base, the second x-ray detector being positioned on the second arm at a location spaced from the second articulation point.

11. The method of claim 10, wherein the first and second arms articulate independently of one another.

12. The method of claim 7, further comprising capturing images of the surface using a visual camera.

13. The method of claim 7, wherein articulating the first segment with respect to the second segment comprises rotating the first segment with respect to the second segment about at least two axes of rotation.

14. A method of interrogating a surface of a structure using an x-ray backscatter system to generate an image of an object obscured behind the surface, the x-ray backscatter system including a mobile base portion, at least a first arm secured to the base at an articulation point, at least one x-ray source, and at least one x-ray detector configured to collect x-rays backscattered from the object, the method comprising:
   a) advancing the system through the structure;
   b) articulating the arm and the x-ray detector about the articulation point, the x-ray detector being positioned on the arm at a location spaced from the articulation point;
   c) generating x-rays from the x-ray source and directing the x-rays toward the surface; and
   c) detecting a portion of the x-rays at the x-ray detector after the portion of the x-rays have been backscattered from the object obscured behind the surface;
   wherein the arm includes a counterweight at a location spaced from the detector and on an opposite side of the articulation point from the detector.

15. The method of claim 14, wherein steps a) through d) are performed simultaneously.

16. The method of claim 14, wherein articulating the arm and the x-ray detector about the articulation point comprises rotating the arm and the x-ray detector about at least two axes of rotation.

17. The method of claim 14, further comprising articulating a second arm and a second x-ray detector about a second articulation point on the base, the second x-ray detector being positioned on the second arm at a location spaced from the second articulation point.

18. The method of claim 17, wherein the first and second arms articulate independently of one another.

19. The method of claim 14, further comprising capturing images of the surface using a visual camera.

20. A method of interrogating a surface of a structure using an x-ray backscatter system to generate an image of an object obscured behind the surface, the x-ray backscatter system including a mobile base portion, at least a first arm secured to the base at an articulation point, at least one x-ray source, and at least one x-ray detector configured to collect x-rays backscattered from the object, the method comprising:
   a) advancing the system through the structure;
   b) articulating the arm, the x-ray detector and the x-ray source about the articulation point, the x-ray detector and the x-ray source being positioned on the arm at locations spaced from the articulation point;
   c) generating x-rays from the x-ray source and directing the x-rays toward the surface; and
   d) detecting a portion of the x-rays at the x-ray detector after the portion of the x-rays have been backscattered from the object obscured behind the surface.

21. The method of claim 20, wherein steps a) through d) are performed simultaneously.

22. The method of claim 20, wherein articulating the arm and the x-ray detector about the articulation point comprises rotating the arm and the x-ray detector about at least two axes of rotation.

23. The method of claim 20, further comprising articulating a second arm and a second x-ray detector about a second articulation point on the base, the second x-ray detector being positioned on the second arm at a location spaced from the second articulation point.

24. The method of claim 23, wherein the first and second arms articulate independently of one another.

25. The method of claim 20, further comprising capturing images of the surface using a visual camera.

* * * * *